United States Patent
Hacke et al.

(10) Patent No.: US 7,559,323 B2
(45) Date of Patent: Jul. 14, 2009

(54) DISPOSABLE MASK ASSEMBLY WITH EXHAUST FILTER

(75) Inventors: Gerhard A. Hacke, Erin (CA); Cornel C. Hacke, Guelph (CA); Martin P. Foley, London (CA)

(73) Assignee: Respan Products, Inc., Ontario (CA)

( * ) Notice: Subject to any disclaimer, the term of this patent is extended or adjusted under 35 U.S.C. 154(b) by 418 days.

(21) Appl. No.: 11/269,678

(22) Filed: Nov. 9, 2005

(65) Prior Publication Data

US 2007/0101990 A1    May 10, 2007

(51) Int. Cl.
*A62B 7/10* (2006.01)
*A62B 23/02* (2006.01)

(52) U.S. Cl. .............................. 128/201.25; 128/206.12

(58) Field of Classification Search ............ 128/205.27, 128/205.25, 206.12, 206.16, 206.27, 206.28, 128/206.15, 201.23, 202.27
See application file for complete search history.

(56) References Cited

U.S. PATENT DOCUMENTS

| | | | | | |
|---|---|---|---|---|---|
| 2,139,137 | A | * | 12/1938 | Schwartz | 128/206.17 |
| 2,153,437 | A | * | 4/1939 | Schwartz | 128/206.17 |
| 2,505,173 | A | * | 4/1950 | Conley | 128/206.15 |
| 2,744,523 | A | * | 5/1956 | Malcom, Jr. et al. | 128/206.17 |
| 2,744,524 | A | * | 5/1956 | Whipple | 128/206.17 |
| 2,744,525 | A | * | 5/1956 | Whipple | 128/206.15 |
| 2,843,121 | A | | 7/1958 | Hudson | |
| 3,142,549 | A | * | 7/1964 | Klusewitz et al. | 96/121 |
| 3,161,491 | A | * | 12/1964 | Gongoll et al. | 96/416 |
| 3,266,490 | A | * | 8/1966 | Klinger et al. | 128/206.15 |
| D250,047 | S | * | 10/1978 | Lewis et al. | D24/110.1 |
| 4,179,274 | A | * | 12/1979 | Moon | 55/524 |
| 4,201,205 | A | * | 5/1980 | Bartholomew | 128/205.25 |
| 4,207,882 | A | * | 6/1980 | Lemere | 128/206.15 |
| 4,328,797 | A | * | 5/1982 | Rollins et al. | 128/202.27 |
| 4,440,163 | A | | 4/1984 | Spergel | |
| 4,588,631 | A | * | 5/1986 | Clark | 428/166 |
| 4,649,912 | A | * | 3/1987 | Collins | 128/202.13 |
| 4,657,010 | A | * | 4/1987 | Wright | 128/205.25 |
| 4,846,166 | A | * | 7/1989 | Willeke | 128/200.24 |
| 4,850,346 | A | * | 7/1989 | Michel et al. | 128/206.15 |
| 4,934,361 | A | * | 6/1990 | Michel et al. | 128/206.17 |
| 4,960,121 | A | * | 10/1990 | Nelson et al. | 128/206.24 |
| 5,117,821 | A | * | 6/1992 | White | 128/206.15 |
| 5,143,061 | A | * | 9/1992 | Kaimer | 128/206.24 |
| 5,181,507 | A | * | 1/1993 | Michel et al. | 128/201.25 |
| 5,222,488 | A | * | 6/1993 | Forsgren | 128/201.25 |
| 5,226,412 | A | | 7/1993 | Winters | |
| 5,240,479 | A | * | 8/1993 | Bachinski | 96/17 |

(Continued)

*Primary Examiner*—Danton DeMille
(74) *Attorney, Agent, or Firm*—Roylance, Abrams, Berdo & Goodman, L.L.P.

(57) ABSTRACT

A face mask assembly and method of assembling a face mask is provided for a patient that includes a face piece sized to fit over the patient's nose and mouth. The face mask assembly forms a mask chamber between the face piece and the patient's nose and mouth. An inhalation adapter is coupled to the face piece to deliver medication to the chamber. A filter housing is coupled to the face piece and includes a flange section that defines a passageway to connect the mask chamber and the flange section. A filter is positioned in the filter housing. A cover is coupled to the flange section and has an exhalation opening or vent to allow gases from the mask chamber to pass through the filter and escape from the passageway to the atmosphere.

21 Claims, 2 Drawing Sheets

U.S. PATENT DOCUMENTS

| | | | |
|---|---|---|---|
| 5,374,458 A * | 12/1994 | Burgio | 428/36.1 |
| 5,474,060 A * | 12/1995 | Evans | 128/204.22 |
| 5,492,114 A * | 2/1996 | Vroman | 128/205.13 |
| 5,505,197 A * | 4/1996 | Scholey | 128/206.17 |
| 5,579,761 A | 12/1996 | Yuschak et al. | |
| 5,647,356 A | 7/1997 | Osendorf et al. | |
| 5,651,810 A * | 7/1997 | Flaherty et al. | 95/287 |
| 5,758,642 A * | 6/1998 | Choi | 128/206.21 |
| 5,776,213 A * | 7/1998 | Flaherty et al. | 55/482 |
| 6,055,983 A * | 5/2000 | Metzger | 128/206.17 |
| 6,298,849 B1 | 10/2001 | Scholey et al. | |
| 6,363,934 B2 * | 4/2002 | Metzger | 128/206.16 |
| 6,418,929 B1 * | 7/2002 | Norfleet | 128/207.11 |
| 6,457,473 B1 * | 10/2002 | Brostrom et al. | 128/207.11 |
| 6,497,232 B2 * | 12/2002 | Fecteau et al. | 128/207.11 |
| 6,584,976 B2 | 7/2003 | Japuntich et al. | |
| 6,659,102 B1 | 12/2003 | Sico | |
| 6,701,925 B1 * | 3/2004 | Resnick | 128/206.17 |
| 6,718,982 B2 * | 4/2004 | Smith et al. | 128/207.12 |
| 6,732,733 B1 * | 5/2004 | Brostrom et al. | 128/206.27 |
| 6,783,566 B2 * | 8/2004 | Estkowski | 55/418 |
| 6,800,225 B1 * | 10/2004 | Hagmann et al. | 264/1.36 |
| 6,854,464 B2 * | 2/2005 | Mukaiyama et al. | 128/206.17 |
| 7,093,596 B2 * | 8/2006 | Muller et al. | 128/206.17 |
| 7,114,498 B1 * | 10/2006 | Nashed | 128/205.27 |
| 2001/0035181 A1 * | 11/2001 | Elkins | 128/200.21 |
| 2002/0078953 A1 * | 6/2002 | Fecteau et al. | 128/202.27 |
| 2002/0162556 A1 * | 11/2002 | Smith et al. | 128/207.12 |
| 2002/0189616 A1 * | 12/2002 | Wolf | 128/205.25 |
| 2003/0127101 A1 * | 7/2003 | Dennis | 128/206.21 |
| 2003/0154984 A1 * | 8/2003 | Fernandes | 128/205.27 |
| 2004/0079373 A1 * | 4/2004 | Mukaiyama et al. | 128/205.27 |
| 2004/0084048 A1 | 5/2004 | Stenzler et al. | |
| 2005/0121029 A1 * | 6/2005 | Reisman | 128/201.22 |
| 2007/0101990 A1 * | 5/2007 | Hacke et al. | 128/201.25 |

* cited by examiner

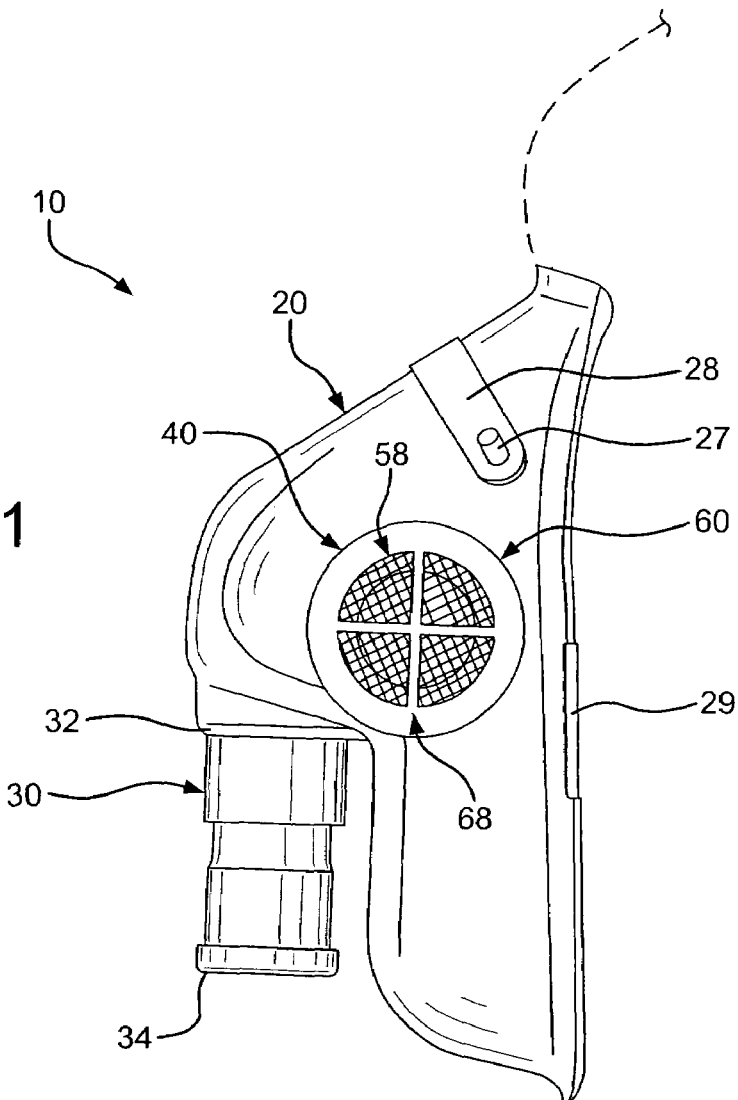
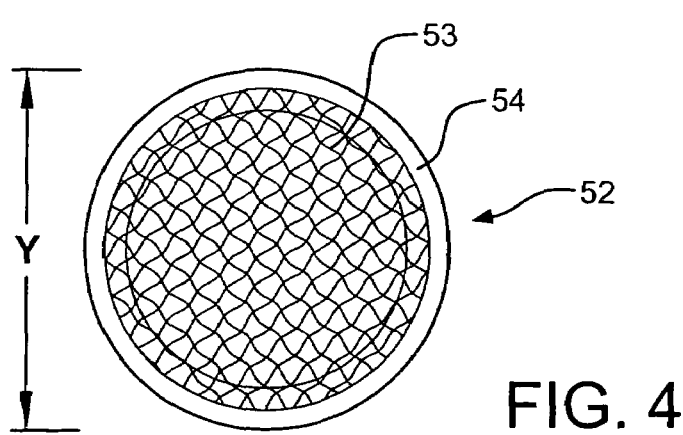

DISPOSABLE MASK ASSEMBLY WITH EXHAUST FILTER

FIELD OF THE INVENTION

The present invention relates to a face mask assembly to filter a patient's exhalation. More particularly, the present invention relates to a face mask assembly including a face piece having a filter positionable between a filter housing and a snap-fitting cover with an exhalation vent. The filter housing also is snap-fitted to the mask face piece.

BACKGROUND OF THE INVENTION

Breathing masks configured to administer gases (e.g. aerosol or oxygen) to a patient have been available for many years. However, these prior art devices are not entirely acceptable for a variety of reasons.

For example, U.S. Pat. No. 6,659,102 to Sico, the entire disclosure of which is hereby incorporated herein by reference, discloses an oxygen mask filter system for preventing the transmission of disease. The mask has an inhalation valve and a plurality of vent apertures mounted on opposing sides of the mask. Filter members are removably mounted on each side of the mask. The filter members are mounted by a post member having a flanged end. Consequently, the filter system is comparatively complex and utilizes a multitude of moving parts. Moreover, the interchangeability of the mask with multiple filters is relatively limited.

Another mask assembly is described in U.S. Pat. No. 5,579,761 to Yuschak et al., the entire disclosure of which is also hereby incorporated herein by reference. This mask assembly includes a respirator having a face piece and a cartridge receiving structure located on the face piece. The mask assembly uses an inhalation filter. An exhalation filter is not positioned between a flange portion and a cover with an exhalation vent to reduce exposure of harmful agents to others that may be in the same room as the patient using the mask. Therefore, healthcare personnel administering treatments to patients are exposed to free airborne medication mist which potentially causes infectious diseases.

Accordingly, in order to address these disadvantages, there have been various additional attempts to provide mask assemblies to reduce the transfer of bacteria/viruses to or from an infected patient. Examples of mask assemblies are disclosed in U.S. Pat. No. 4,440,163 to Spergel; U.S. Pat No. 4,934,361 to Michel et al.; 5,226,412 to Winters; U.S. Pat No. 5,647,356 to Osendorf et al.; U.S. Pat No. 6,298,849 to Scholey et al.; and U.S. Pat No. 6,584,976 to Japuntich et al., and U.S. Patent Publication No. 2004/0084048 to Stenzler et al.; the disclosures of each are hereby incorporated herein by reference in their entirety. Although some of the features of those mask assemblies ease the disadvantages described above, a continuing need exists for an improved mask assembly which minimizes or eliminates release of patient exhaled gases and/or surplus medication into room air; is readily interchangeable with a number of different types of filters; is relatively simple to use, make, and assemble; and which simultaneously reduces the number of parts necessary for manufacture and assembly.

SUMMARY OF THE INVENTION

An object of the present invention is to solve at least the above problems and/or disadvantages and to provide at least the advantages described below.

Accordingly, an object of the present invention is to provide a filter and a method of assembling a filter that makes it relatively simple to install the filter between the filter housing and a cover.

Another object of the present invention is to provide a mask assembly which reduces the number of parts necessary for manufacture and assembly.

A further object of the present invention is to provide a mask assembly which is readily interchangeable with a number of different types of filters and is relatively simple to make, use, and assemble.

The foregoing objects are attained by providing a face mask assembly for a patient including a face piece sized to fit over the patient's nose and mouth, and forming a mask chamber between the face piece and the patient's nose and mouth; an inhalation adapter coupled to the face piece to deliver a fluid to the chamber; at least one filter housing coupled to the face piece and including a flange section, and defining a passageway to connect the mask chamber to the flange section; at least one filter positioned in the at least one filter housing; and at least one cover coupled to the at least one flange section, and having an exhalation vent to allow gases from the mask chamber to pass through the filter and escape from the passageway to the atmosphere.

The foregoing objects are also attained by providing a face mask assembly for a patient including face piece sized to fit over the patient's nose and mouth, and forming a mask chamber between the face piece and the patient's nose and mouth; an inhalation adapter coupled to the face piece to deliver a fluid to the chamber; at least one filter housing coupled to the face piece including a flange section, and defining a passageway connecting the mask chamber to the flange section; at least one filter positioned in the at least one filter housing; at least one cover coupled to the at least one flange section and having an exhalation vent to allow gases from the mask chamber to pass through the filter and escape from the passageway to the atmosphere.

The foregoing objects are further attained by providing a method of assembling a mask assembly for a patient, comprising the steps of positioning a face piece over the patient's nose and mouth to form a mask chamber between the face piece and the patient's nose and mouth; coupling an inhalation adapter to the face piece to deliver fluid to the mask chamber; arranging at least one filter housing including a flange section, and defining a passageway connecting the mask chamber to the flange portion on the face piece; positioning at least one filter positioned on a top surface of the flange portion of the filter housing; and coupling at least one cover to the at least one flange portion having an exhalation vent to allow gases from the mask chamber to pass through the filter and escape from the passageway to the atmosphere.

Other objects, advantages, and salient features of the invention will become apparent to those skilled in the art from the following detailed description, which, taken in conjunction with the annexed drawings, discloses preferred embodiments of the invention.

BRIEF DESCRIPTION OF THE DRAWINGS

The above and other objects, and features, and advantages of certain embodiments of the present invention will become more apparent from the following description taken in conjunction with the accompanying drawings, which form a part of this application and in which:

FIG. 1 is a side elevational view of a face mask assembly in accordance with an embodiment of the present invention;

FIG. 4 is an enlarged side elevational view of the filter by itself.

Throughout the drawings, the same drawing reference numerals will be understood to refer to the same elements, features, and structures.

DETAILED DESCRIPTION OF THE EXEMPLARY EMBODIMENT

Figure 2:
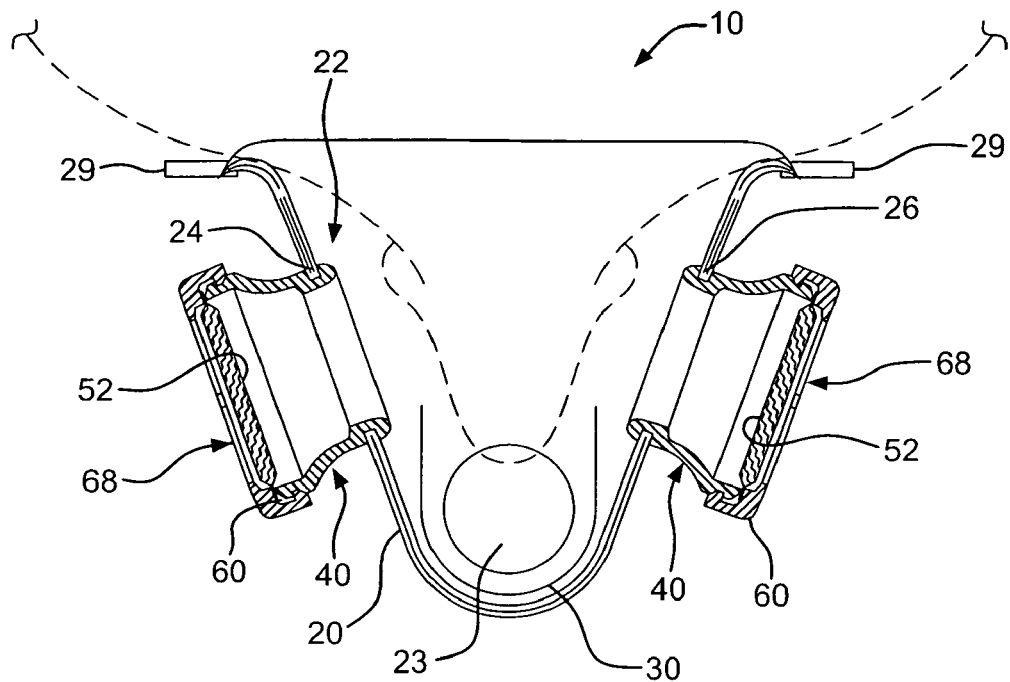
FIG. 2 is a top plan view in partial cross-section of the face mask assembly shown in FIG. 1.

Referring to FIGS. 1-4, a face mask assembly 10 in accordance with an embodiment of the present invention is shown. The face mask assembly 10 includes a face piece 20 and an inhalation adapter 30. The mask assembly also includes a filter housing 40, a filter 52, and a cover 60 on each side.

Figure 3:
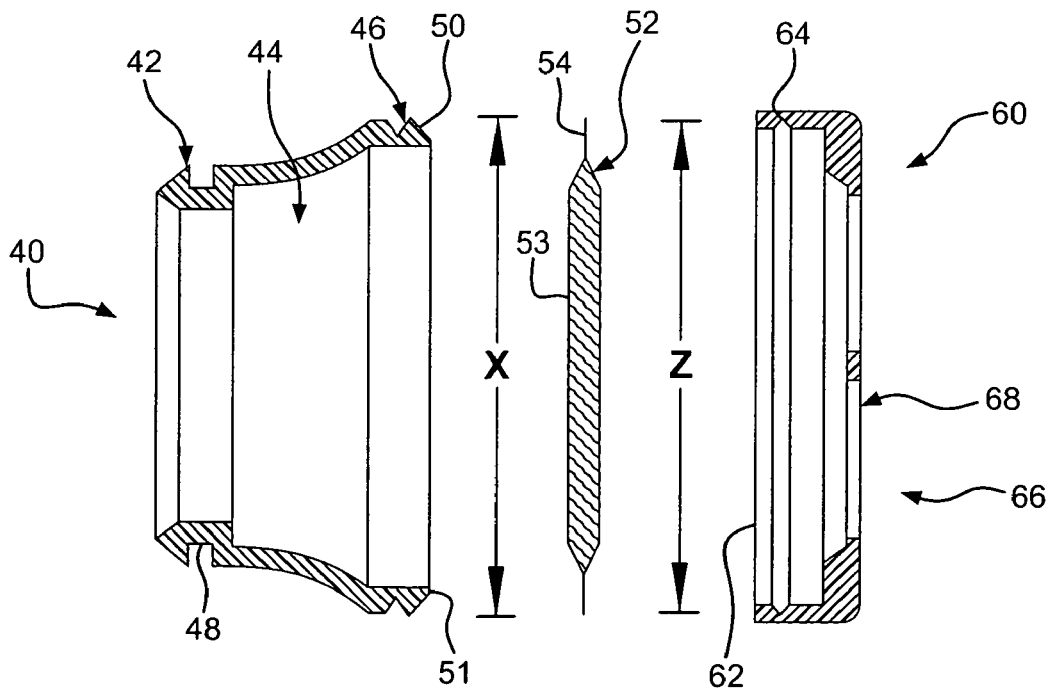
FIG. 3 is an enlarged and exploded top plan view in cross-section of a filter housing, filter, and cover of the face mask assembly shown in FIGS. 1-2.

As best seen in FIGS. 1-3, the face piece 20 preferably comprises a substantially curvilinear shaped shell configured to fit over the nose and mouth of a patient to establish a seal. As shown in FIG. 2, a breathing mask chamber 22 is formed between an inner surface of the face piece 20 and the nose and mouth of the patient. Preferably, a lower portion of the face piece is provided with an inhalation aperture 23. The inhalation aperture 23 enables a supply of air to travel into the mask chamber 22 from the inhalation adapter 30. Apertures 24 and 26 extend through the face piece 20 to receive a neck portion 42 (FIG. 3) of the two filter housings 40 via a snap fit. The apertures 24 and 26 fluidly connect the mask chamber 22 with a passageway 44 (FIG. 3) of the two filter housings 40. The apertures 24 and 26 preferably are substantially circular in shape; however, other suitable shapes and sizes may be used.

A portion of the face piece 20 is upturned. This upturned portion of the face piece is preferably substantially triangularly shaped to accommodate engagement with the bridge of a patient's nose as seen in FIGS. 1 and 2.

Turning to FIG. 1, one or more projections 27 are arranged on the outer surface of the face piece 20 proximate to the upturned portion. These projections 27 extend outwardly from the face piece and are configured to extend through apertures of a nose clip 28. The nose clip 28 enables the face piece 20 to adapt to a multitude of varying shaped nose bridges. Thus, a proper seal may be maintained within the mask chamber 22. As best seen in FIG. 1, the projections 27 are preferably upstanding, substantially cylindrical supports, and the apertures are preferably cylindrical; however, other suitable arrangements, sizes, and shapes may be used. The nose clip 28 is preferably a strip of resilient material such as aluminum.

At least two edges of the face piece 20 are provided with substantially polygonal shaped ears 29 (FIGS. 1 and 2). The ears 29 are preferably provided with apertures for receiving an engagement portion of a retaining strap (not shown); however, other suitable arrangements and constructions may be used. For example, alternatively, the retaining strap may have apertures and the ears 29 may have the engagement portion. The retaining strap is preferably made of a resilient material and adjustable. Thus, the length of the retaining strap may be adjusted for accommodating a multitude of patients' faces to establish a proper seal.

The face piece 20 is preferably constructed of a substantially light-weight, resilient, inert, and fire-resistant material such as, but not limited to, a rubber or plastic material. The face piece 20 is preferably relatively thin in cross-section so as to be soft and flexible. The face piece 20 is also preferably strong enough to resist the stress imposed thereon by the weight of the other components suspended therefrom.

As best seen in FIG. 1, the conventional inhalation adapter 30 has first and second open ends 32 and 34. The first end 32 of the inhalation adapter 30 is coupled to the face piece 20 via the inhalation aperture 23. The second end 34 of the inhalation adapter 30 may be configured to act as a plenum for a fluid supply source such as a pressurized gas bottle containing oxygen. The inhalation adapter 30 may also be used without pressurized gas. The inhalation adapter 30 may solely provide fluid such as aerosolized medication in combination with the oxygenated ambient atmosphere. Detailed descriptions of the inhalation adapter's 30 well-known conventional functions are omitted for clarity and conciseness. Accordingly, the inhalation adapter functions to sustain a breathable atmosphere within the mask chamber 22. The inhalation adapter 30 is preferably formed of a light-weight plastic. The inhalation adapter 30 is preferably coupled (e.g. bonded) to the face piece utilizing dichloromethane.

Turning to FIGS. 2-3, filter housing 40 will now be described. The filter housing 40 has inner and outer surfaces. The inner surface defines a fluid passageway 44. A first end of the filter housing 40 comprises a neck portion 42 and the second end of the filter housing 40 comprises a flange portion 46. The neck portion 44 defines a first opening. The flange portion 46 defines a second opening.

The neck portion 42 of the filter housing 40 includes a substantially annular groove 48 with a substantially U-shaped cross-section located in the outer surface of the filter housing 40. The filter housing 40 is preferably secured via a snap fit to the face piece 20 by forcing the neck portion 42 through the apertures 24 and 26 in the face piece 20 with a slight interference fit. Thus, groove 48 has a diameter slightly larger than the diameters of apertures 24 and 26, and engages the side edges of the apertures 24 and 26, thereby securing the filter housing 40 to the face piece 20. It is preferable that the width of the filter housing 40 increases from the neck portion 42 to the flange portion 46. Consequently, the width of the fluid passageway 44 gradually increases from the first end of the filter housing 40 to the second end.

The flange portion 46 has a substantially V-shaped annular projection 50 extending in a direction away from the outer surface of the filter housing 40 and has a diameter "x". It is preferable that the V-shaped projection 50 is configured to secure the cover 60 thereto via a snap fit. As stated above, since the outer surface of the filter housing 40 preferably expands outwardly from the neck portion 42, the flange portion 46 of the filter housing 44 has a predetermined width that is greater than the width of the neck portion 40 to accommodate engagement with the filter 52 on a top surface 51 thereof as described in further detail below and seen in FIGS. 1-4.

The filter housing 40 is preferably polypropylene injection molded and substantially cylindrical in shape. The filter housing 40 is preferably resilient and flexible to facilitate pushing of the neck portion 42 through the face piece 20 apertures 24 and 26. It should be understood that other suitable arrangements and constructions may be used.

The substantially disc-shaped filter 52 is best seen in FIG. 3. The middle portion 53 of the filter 52 has a substantially uniform cross-section. The filter 52 also has side edges, which gradually taper to a peripheral annular rim 54. A diameter "y" of the filter 52 rim 54 is about the same size as the diameter "x" of the flange portion 46 so that the filter 52 rim 54 engages the top surface 51 of the flange portion 46. The filter 52 is arranged so that it is positioned between the filter housing 40 and the cover 60 and simply secured thereto via engagement of the cover 60 on the housing 40 as described in further detail below and seen in FIGS. 1-4. Thus, fluid traveling through the fluid passageway 44 travels through the filter 52. Preferably a conventional electrostat filter 52 is utilized having permanent electrostatic charges to remove airborne particles. Such a filter 52 generally includes a uniform web of charged fibers to enable the media to capture particles throughout the depth of the filter 52 rather than only on the surface. The filter 52 is preferably for medical applications including anaesthetic gas/respiratory care, pulmonary function/spirometry and incubator filters. An example of such a filter 52 is the Ahlstrom Electrostat Filter Media HP150/410.

Turning to FIG. 3, the cover 60 is preferably substantially annular in shape. The cover 60 has an inner wall, an outer wall, a first end, and a second end. The first end defines a first opening 62 having a predetermined diameter. Disposed along the inner wall proximate the first opening is an annular groove 64 with a substantially V-shaped cross section having a maximum diameter "z" which is slightly smaller than diameter "x" of flange portion 46. This allows the cover 40 to snap fit over the flange portion 46 and stay secured thereto while keeping the filter rim 54 sandwiched and rigidly secured therebetween. The inner wall is substantially L-shaped. The inner wall extends upwardly from the first end, then inwardly, and then again upwardly to define the second opening or exhalation vent 66 in the second end. The second opening 66 also has a predetermined diameter that is preferably smaller than the width of the first opening 62. The second opening 66 is spanned by an X-shaped brace 68, which is integrally formed with cover 60 and helps to keep the filter 52 in place. The exhalation vent 68 has a plurality of openings. The type of fluid medium utilized determines the number and size of the openings for the brace 68.

The opening 66 acts as a vent to exhaust the gas contents within the mask chamber 22 to the ambient atmosphere. The filter 52 is positioned between the flange portion 46 of the filter housing 40 and the cover 60 having opening 66. Thus, the exhalation of toxic elements from the mask chamber 22 is minimized or eliminated and healthcare personnel are protected. Additionally, the rebreathing of medication aerosol deposited on filters may improve the medication delivery efficiency to the patient. The cover 60 is also preferable constructed of resilient polypropylene and injection molded.

ASSEMBLY AND OPERATION

Assembly and operation of the face mask assembly 10 in accordance with an exemplary embodiment of the present invention will now be described with reference to FIGS. 1-4.

As best seen in FIGS. 1-4, the filter 52 is first positioned between the filter housing 40 and the cover 60 by snap fitting the two components together. More specifically, the peripheral rim 54 of the filter 52 is secured between the top surface 51 of the flange portion 46 and the inner wall of the cover 60. The substantially V-shaped groove 64 of the cover 60 engages the substantially V-shaped projection 50 of the flange portion 48 to establish a snap-fit connection. Thus, the filter 52 is secured between the filter housing 40 and the cover 60. Lastly, the filter housing 40 is secured to the face piece 20 by pushing the neck portion 42 through the face piece 20 apertures 24 and 26.

Once the mask assembly 10 is constructed and mounted in the desired location on the face piece 22, as hereinbefore described, the apparatus may function by supplying and maintaining a breathable atmosphere within the mask chamber 22. A sufficient supply of fluid available from a pressurized gas source or from the oxygenated air travels through the inhalation adapter 30. The fluid may be mixed with another suitable medium such as aerosolized medicine. For example, aerosolized medication treatment (e.g. Bronchial diluters) and/or oxygen may be provided to patients. The fluid is introduced into the mask chamber 22 via the inhalation aperture 23 in the face piece 22. One or more filter housings 40 allow air to exhaust from the mask chamber 22 through the filter 52 and opening 66 when the patient exhales, thereby maintaining a constant, atmospheric pressure within the mask chamber 22.

The filter 52 secured in the filter housing 40 minimizes or eliminates release of toxins in a patient's exhaled gases and/or surplus aerosolized medication into the ambient air. The device will therefore greatly minimize or eliminate the transfer of bacteria/viruses from an infected patient to healthcare personnel. Interchangeability of the mask assembly 10 is also comparatively easier due to the simple assembly of the filter housing 40 and cover 60. In addition, due to increasing numbers of newly developed aerosol type medications with significant toxicity levels, exposure of healthcare personnel (respiratory therapists, nurses, etc.) administering treatments to patients to free airborne medication mist will be minimized or eliminated. Therefore, the device is of interest to healthcare providers due to the inception of SARS and other infectious respiratory tract diseases.

While the invention has been shown and described with reference to certain embodiments thereof, it will be understood by those skilled in the art that various changes in form and details may be made therein without departing from the spirit and scope of the invention as defined by the appended claims.

What is claimed is:

1. A face mask assembly for a patient, comprising:
   a face piece sized to fit over the patient's nose and mouth, and forming a mask chamber between said face piece and the patient's nose and mouth;
   an inhalation adapter coupled to said face piece to deliver a fluid to said chamber;
   at least one filter housing coupled to said face piece including a flange portion, and defining a passageway connecting said mask chamber to said flange portion; and
   at least one filter having first and second side edges tapering towards an annular rim disposed between said at least one filter housing and at least one cover, wherein said at least one cover is snap-fitted over said flange portion and having said filter rim sandwiched therebetween, and having an exhalation vent to allow gases from said mask chamber to pass through said filter and escape from said passageway to the atmosphere.

2. A face mask assembly according to claim 1, wherein said at least one filter housing is removably coupled to said face piece.

3. A face mask assembly according to claim 1, wherein a width of said at least one filter is greater than a width of said flange portion, so that said at least one filter engages a top surface of said flange portion.

4. A face mask assembly according to claim 1, wherein projections are arranged on said face piece to receive a nose clip.

5. A face mask assembly according to claim 1, wherein said rim engages a top surface of said flange portion.

6. A face mask assembly according to claim 1, wherein said filter is secured to said filter housing with an engagement of said cover.

7. A face mask assembly according to claim 1, wherein said cover includes an inner wall, an outer wall, a first end, and a second end wherein said first end defines a first opening.

8. A face mask assembly according to claim 7, wherein said inner wall is L-shaped.

9. A face mask assembly according to claim 7, wherein said first opening includes an annular wall with a substantially V-shaped cross-section.

10. A face mask assembly according to claim 9, wherein said cross-section has a maximum diameter "z".

11. A face mask assembly according to claim 10, wherein said maximum diameter "z" is less than a diameter "x" of said flange portion.

12. A face mask assembly for a patient, comprising:
a face piece having at least one opening and forming a mask chamber between said face piece and the patient's nose and mouth;
an inhalation adapter coupled to said face piece to deliver a fluid to said chamber;
at least one filter housing snap-fitted to said at least one opening, said filter housing including a flange portion, and defining a passageway connecting said mask chamber to said flange portion; and
at least one filter having first and second side edges tapering towards an annular rim disposed between said at least one filter housing and at least one cover, wherein
said at least one cover is snap-fitted over said flange portion and having said filter rim sandwiched therebetween, and having an exhalation vent to allow gases from said mask chamber to pass through said filter and escape from said passageway to the atmosphere.

13. A face mask assembly according to claim 12, wherein a width of said at least one filter is greater than a width of said flange portion, so that said at least one filter engages a top surface of said flange portion.

14. A face mask assembly according to claim 12, wherein projections are arranged on said face piece to receive a nose clip.

15. A face mask assembly according to claim 12, wherein said rim engages a top surface of said flange portion.

16. A face mask assembly according to claim 12, wherein said filter is secured to said filter housing with an engagement of said cover.

17. A face mask assembly according to claim 12, wherein said cover includes an inner wall, an outer wall, a first end, and a second end wherein said first end defines a first opening.

18. A face mask assembly according to claim 17, wherein said inner wall is L-shaped.

19. A face mask assembly according to claim 17, wherein said first opening includes an annular wall with a substantially V-shaped cross-section.

20. A face mask assembly according to claim 19, wherein said cross-section has a maximum diameter "z".

21. A face mask assembly according to claim 20, wherein said maximum diameter "z" is less than a diameter "x" of said flange portion.

* * * * *